(12) United States Patent
Tamai

(10) Patent No.: US 7,049,969 B2
(45) Date of Patent: May 23, 2006

(54) LIQUID DETECTION SENSOR AND LIQUID DETECTION APPARATUS

(75) Inventor: Seiichiro Tamai, Toyono-gun (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/641,066

(22) Filed: Aug. 15, 2003

(65) Prior Publication Data

US 2004/0036484 A1    Feb. 26, 2004

(30) Foreign Application Priority Data

Aug. 23, 2002    (JP)    ............................. 2002-244301

(51) Int. Cl.
*G08B 23/00*    (2006.01)
(52) U.S. Cl. ............... 340/573.5; 340/572.4; 340/572.5; 340/604; 340/686.1
(58) Field of Classification Search ............ 340/572.5, 340/602, 603, 604, 605, 573.5, 572.1, 686.1, 340/572.4; 128/886; 200/61.04, 61.05; 604/361; 343/895, 866, 741; 324/663
See application file for complete search history.

(56) References Cited

U.S. PATENT DOCUMENTS 5,903,222 A * 5/1999 Kawarizadeh et al. ...... 340/604
6,384,728 B1 * 5/2002 Kanor et al. ............. 340/573.1
6,559,772 B1 * 5/2003 Zand et al. ................. 340/604
6,774,800 B1 * 8/2004 Friedman et al. ........ 340/573.5
6,809,703 B1 * 10/2004 Serra .......................... 343/895
2003/0145073 A1 * 7/2003 Fukushima et al.

FOREIGN PATENT DOCUMENTS

| JP | 55-97446 | 7/1980 |
| JP | 59-117944 | 8/1984 |
| JP | 60-213857 | 10/1985 |
| JP | 3-25177 | 5/1991 |
| JP | 11-056890 | 3/1999 |
| JP | 2001-161732 | 6/2001 |
| JP | 2001-289775 | 10/2001 |
| JP | 2001-325865 | 11/2001 |
| JP | 2002-224151 | 8/2002 |

* cited by examiner

*Primary Examiner*—Hung Nguyen
(74) *Attorney, Agent, or Firm*—Wenderoth, Lind & Ponack, L.L.P.

(57) ABSTRACT

A moisture detection sensor includes a resonant circuit composed of an antenna coil 53 and a capacitor C. A noncontact tag composed of covering materials 51 and 57 covers the resonant circuit. The capacitor C has a pair of electrodes 52 and 56 and a dielectric 55 interposed between the electrodes 52 and 56, and the covering material 57 contains a through-hole 57a that allows the liquid to infiltrate into the dielectric 55 from outside.

24 Claims, 15 Drawing Sheets

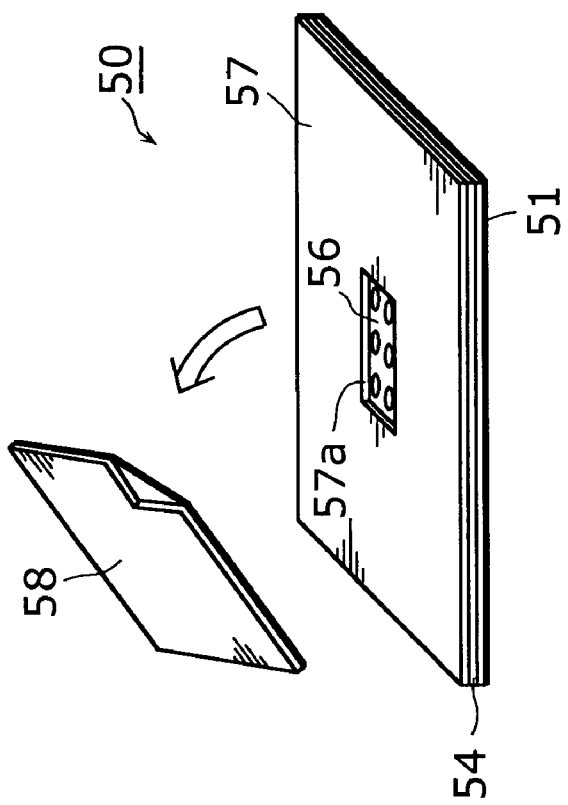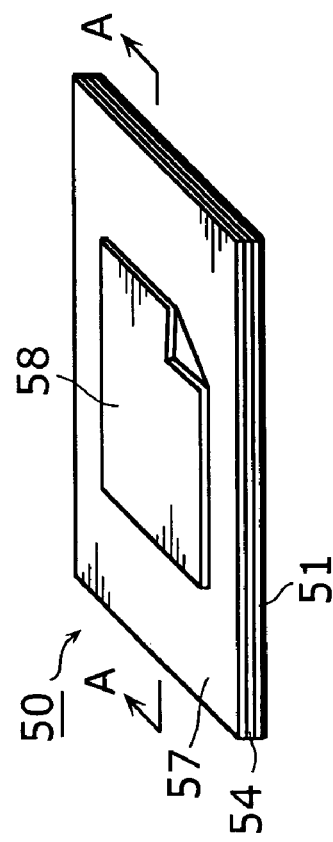

LIQUID DETECTION SENSOR AND LIQUID DETECTION APPARATUS

BACKGROUND OF THE INVENTION (1) Field of the Invention

The present invention relates to a liquid detection sensor, a liquid detection apparatus, and a liquid detection system using the sensor and the apparatus.

(2) Description of the Related Art

Along with recent aging society, various care supplies such as paper diapers and apparatuses detecting incontinence have been developed. As one of the apparatuses, for example, the Japanese Laid Open Patent Nos. 2001-289775 and 2001-325865 disclose a liquid detection sensor using a noncontact tag method and a liquid detection apparatus that detects a state of the liquid detection sensor without contacting the sensor.

The liquid detection sensor disclosed in the above documents comprises a coil L, a capacitor C and a switch SW, and has a configuration example in which these components are connected in series in a loop shape (hereinafter this configuration example is referred to as a "first conventional configuration example"), and another configuration example in which the coil L and the capacitor C are connected in a loop shape, and the switch SW is connected to the capacitor C in parallel (hereinafter this configuration example is referred to as a "second conventional configuration example").

The switch SW of the liquid detection sensor shown in the first and the second conventional configuration examples includes a metal board having electrical conductivity and flexibility like a flat spring, a metal board having electrical conductivity, an insulator located between ends of the metal boards, a material such as paper or fiber, of which volume is reduced when absorbing water, and so on. The switch SW is structured to maintain both electrodes in a normally open state at an initial stage (when dry), and switches both electrodes into a conducting state when absorbing liquid (moisture such as water).

Therefore, in the liquid detection sensor according to the first conventional configuration example, a resonant circuit is not formed by the coil L and the capacitor C because the switch SW cuts out the conduction at its initial stage. The resonant circuit is formed only when the material, which reduces its volume with water, absorbs water, and the switch SW switches into the conducting state. Contrary to the first conventional configuration example, a resonant circuit in the liquid detection sensor according to the second conventional configuration example is formed by the coil L and the capacitor C when the switch SW cuts out the conduction at the initial stage, and the resonant circuit disappears when the material, which reduces its volume with water, absorbs water and the switch SW switches into the conducting state.

In the initial state of the first conventional configuration example, when a detection radio wave at a resonant frequency is sent from the liquid detection apparatus, a receiving level of the radio wave coming back from the liquid detection sensor does not fall since the resonant circuit is not yet formed. But, when the material that reduces its volume absorbs water and the switch SW switches into the conducting state, the receiving level of the radio level coming back from the liquid detection sensor drops. On the other hand, as the resonant circuit is formed in the initial state of the second conventional configuration example, the receiving level of the radio wave coming back from the liquid detection sensor falls. And, when the material that reduces its volume absorbs water and the switch SW switches into the conducting state, the resonant circuit disappears. Consequently, the receiving level of the radio wave coming back from the liquid detection sensor goes up.

Therefore, even if either of the liquid detection sensors in the first and the second conventional examples is used, it is easy for the liquid detection apparatus to detect a condition of the liquid detection sensor by monitoring two different values in the receiving level of the radio wave at the resonant frequency.

However, because the conventional liquid detection sensors are structured to have a switch SW having a complex configuration, it becomes costly as it gets bigger. Also, paper, fiber or the like is used for the material that reduces its volume when absorbing water in the switch SW. Therefore, once the material absorbs water, it does not restore its original volume as it looses elasticity. Therefore, even when the material that reduces its volume dries out, both flat springs are conductive. As a result, the expensive liquid detection sensor cannot be reused.

Moreover, in the conventional liquid detection apparatus, a detection radio wave at a specific resonant frequency is emitted, and two different values in the receiving level of the radio wave at the resonant frequency are monitored. Therefore, when the resonant frequency of the liquid detection sensor scatters and deviates from the specific resonant frequency of the radio wave, which is emitted from the liquid detection apparatus, the level of the radio wave coming back from the liquid detection sensor does not change in the resonant frequency of the detection electric field emitted from the liquid detection apparatus. Consequently, because a subtle level change cannot be detected with the conventional method that compares two values in the liquid detection apparatus, it is not possible to accurately detect the condition of the liquid detection sensor.

SUMMARY OF THE INVENTION

A primary objective of the present invention is to provide a liquid detection sensor which is small, inexpensive and reusable.

A secondary objective of the present invention is to provide a liquid detection apparatus which can accurately detect a condition of the liquid detection sensor even when a resonant frequency of the liquid detection sensor is dispersed.

In order to achieve the primary objective, the liquid detection sensor related to the present invention is a liquid detection sensor that detects liquid, comprising: a resonant circuit composed of an antenna coil and a capacitor; and a noncontact tag composed of a covering material that covers the resonant circuit. The capacitor has a pair of electrodes and a dielectric interposed between the electrodes, and the covering material has a through-hole that allows the liquid to infiltrate into the dielectric from outside.

Therefore, any conventional type of switch is not necessary, so that the liquid detection sensor can be structured as a compact and inexpensive one. Besides, since there is no situation in which the switch leaves the state conductive, the liquid detection sensor can be reused.

To be more specific, the present invention may have a configuration in which at least one of the electrodes has a pore that communicates with the through-hole.

Because of this, it is possible to make a fluctuation, which is between a dielectric constant when the dielectric is dry and a dielectric constant when the dielectric gets wet due to liquid inflow, bigger in a short time, and it can prevent the liquid detection sensor from delaying its liquid detection. Also, it can hasten a drying process of the dielectric for recycling.

To accomplish the above secondary objective, the liquid detection apparatus is a liquid detection apparatus that wirelessly detects a condition of a liquid detection sensor composed of a noncontact tag and attached to an object to be checked. The liquid detection apparatus comprises: a detection radio wave emitting unit operable to emit a detection radio wave to the liquid detection sensor when the condition of the liquid detection sensor is detected; a radio wave receiving unit operable to receive a radio wave coming back from the liquid detection sensor when the detection radio wave is emitted; and a decision unit operable to decide, based on a receiving level of the radio wave received by the radio wave receiving unit, wetness or dryness of a dielectric interposed between electrodes of the capacitor.

Therefore, even when the resonant frequency of the liquid detection sensor is dispersed, various comparisons are possible, such as comparison of levels when the resonant circuit is formed, so that the condition of the liquid detection sensor can be accurately detected.

To be specific, the present invention may have a configuration in which the detection radio wave emitting unit sweeps a frequency of the detection radio wave, and the decision unit includes a frequency specifying unit operable to specify a frequency in a case in which the receiving level of the radio wave received by the radio wave receiving unit hits a lowest level, and a frequency fluctuation detecting unit operable to detect a fluctuation in the frequency specified by the frequency specifying unit, and decides the wetness or the dryness based on an amount of the fluctuation in the frequency.

In this way, even when the liquid detection sensor is reused, it is possible to detect the condition of the liquid detection sensor more accurately.

The present invention may be realized as a liquid detection system comprising the above liquid detection sensor and liquid detection apparatus, as a liquid detection method having characteristic means, which forms the liquid detection apparatus, or as a program having a computer or the like to execute a step, which is executed by the liquid detection apparatus. Also, it is obvious that the program may be stored in a recording media such as a DVD and widely distributed.

As mentioned above, according to the present invention, a user who uses the liquid detection system comprising a compact and inexpensive liquid detection sensor and a highly accurate liquid detection apparatus, can, for example, provide appropriate and user-friendly care for the aged by exchanging his diaper quickly through detection of incontinence, or have a pleasant time with plants by watering the plants appropriately through detection of watering needs. Therefore, the present invention makes rapid progress in value provided by the liquid detection system, and practical value of the present invention is extremely high.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings:

FIG. 2 is a diagram showing a mechanical configuration of a moisture detection sensor 50 shown in FIG. 1.

DESCRIPTION OF THE PREFERRED EMBODIMENT(S)

The following describes a liquid detection system related to embodiments of the present invention in detail with reference to diagrams.

First Embodiment

Figure 1:
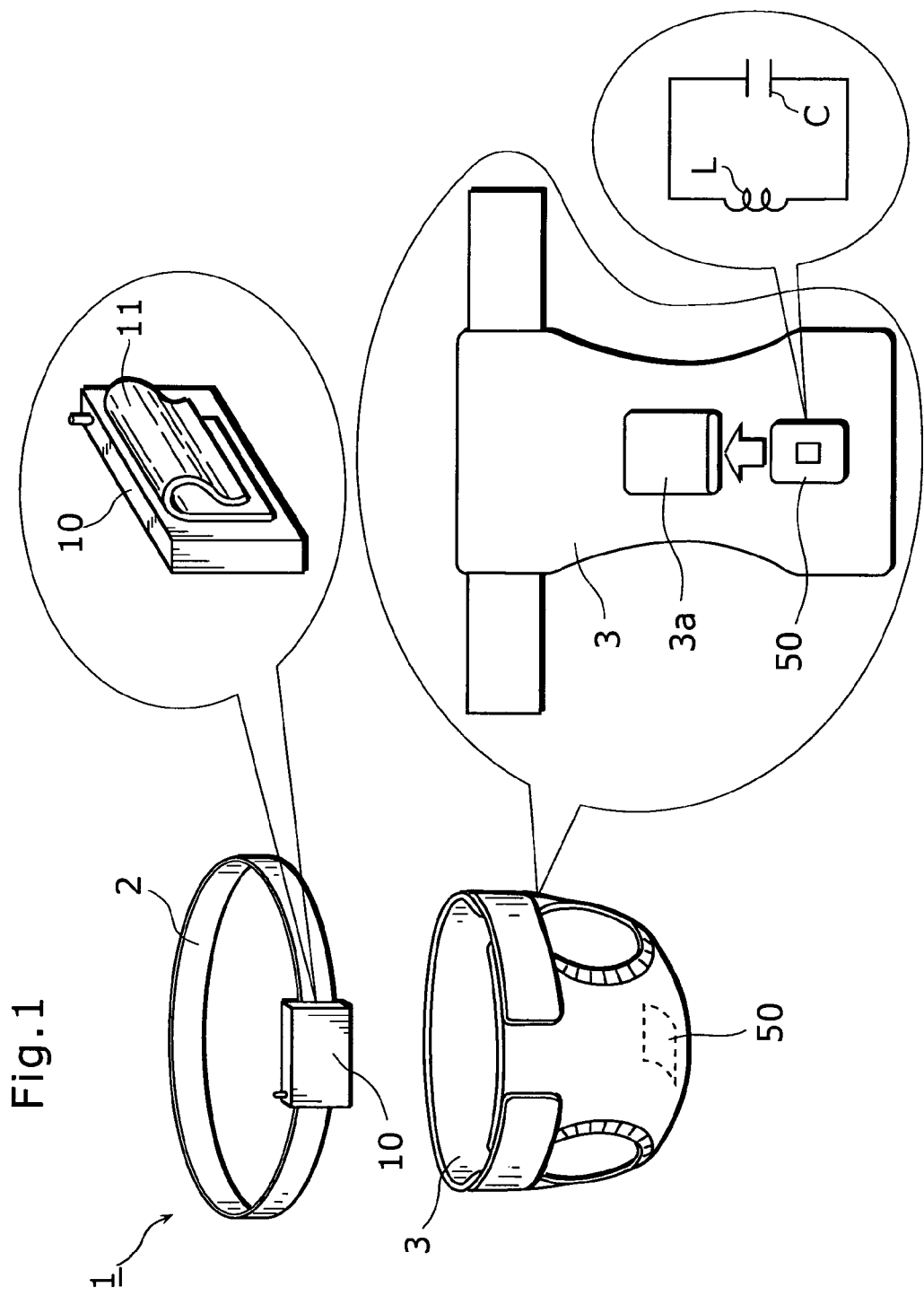
FIG. 1 is a diagram showing an overall configuration for a case in which the liquid detection system related to a first embodiment is applied to detecting incontinence.

FIG. 1 is a diagram showing an overall configuration for a case in which the liquid detection system related to the first embodiment is applied to detecting incontinence.

As shown in the diagram, a moisture detection system (a liquid detection system) 1 comprises a diaper 3, a moisture detection sensor (a liquid detection sensor, a noncontact tag) 50 attached to this diaper 3, a belt 2 and a moisture detection apparatus (a liquid detection apparatus, a tag reader apparatus) 10 attached to this belt 2.

A pocket 3a is provided for attaching the moisture detection sensor 50 at a center part of the diaper 3 where liquid detection is performed, and the moisture detection sensor 50 is inserted into an inside of the pocket 3a from an opening of this pocket 3a. The diaper 3 where the moisture detection sensor 50 is inserted is attached to a person who needs care (a care-recipient) such as a baby or an elderly person. The moisture detection sensor 50 is a noncontact tag including a resonant circuit composed of an antenna coil L and a capacitor C connected in parallel with this antenna coil L, and changes a resonant frequency according to a condition of detecting moisture (liquid).

The belt 2 is attached to the waist of the person who needs care. A clip 11 is attached to the moisture detection apparatus 10. Using the clip 11, the moisture detection apparatus 10 is fixed on the belt 2, which is close to the moisture detection sensor. Instead of the belt 2, a belt-bag may be used and the moisture detection apparatus 10 may be inserted into the belt-bag. In this case, the clip 11 may be omitted, so that the configuration of the moisture detection apparatus 10 can be simplified.

The moisture detection apparatus 10 emits a detection radio wave for detecting moisture to the moisture detection sensor 50 regularly, resonates the resonant circuit of the moisture detection sensor 50 (explained later) through electromagnetic induction by the detection radio wave wirelessly, and detects through the resonant frequency whether the moisture detection sensor 50 is wet by some liquid (urination or defecation) due to incontinence or the like.

FIG. 2 is an external view showing a mechanical configuration of the moisture detection sensor 50 shown in FIG. 1. Especially, FIG. 2 A is a diagram showing an external view of the sensor 50 before it is attached to a pocket of the diaper, and FIG. 2 B is a diagram showing an external view of sensor 50 when it is attached on the pocket of the diaper.

As shown in FIG. 2, the moisture detection sensor 50 comprises a substrate 54 in which the above-mentioned antenna coil L and the capacitor C are formed, a pair of covering materials 51 and 57 respectively affixed on an upper surface and a lower surface of this substrate 54, and a moisture-proof cover 58 (a sealing member) affixed on an upper surface of the covering material 57. The substrate 54 and the covering materials 51 and 57 are thin sheet materials that perform electrical isolation and form a square shape in the same size. In a center part of the covering material 57, a through-hole 57a is formed, which allows liquid to infiltrate into the inside from the outside of the body and to leach out from the inside to the outside.

The moisture-proof cover 58 blocks the through-hole 57a to prevent the dielectric of the capacitor C from absorbing moisture until moisture detection is started. The moisture-proof cover 58 is removed when the moisture detection sensor 50 is attached to the diaper 3 so that the through-hole 57a is opened to allow external moisture to infiltrate into a dielectric 55. Like the covering materials 51 and 57 and the substrate 54, the moisture-proof cover 58 is a thin sheet material performing electrical isolation, and is formed in a square shape which is a little bigger than the through-hole 57a. A fold 58a is formed at a part of the moisture-proof cover 58, so that it is easy to peel the moisture-proof cover 58 from the covering material 57 for detachment.

Figure 3:
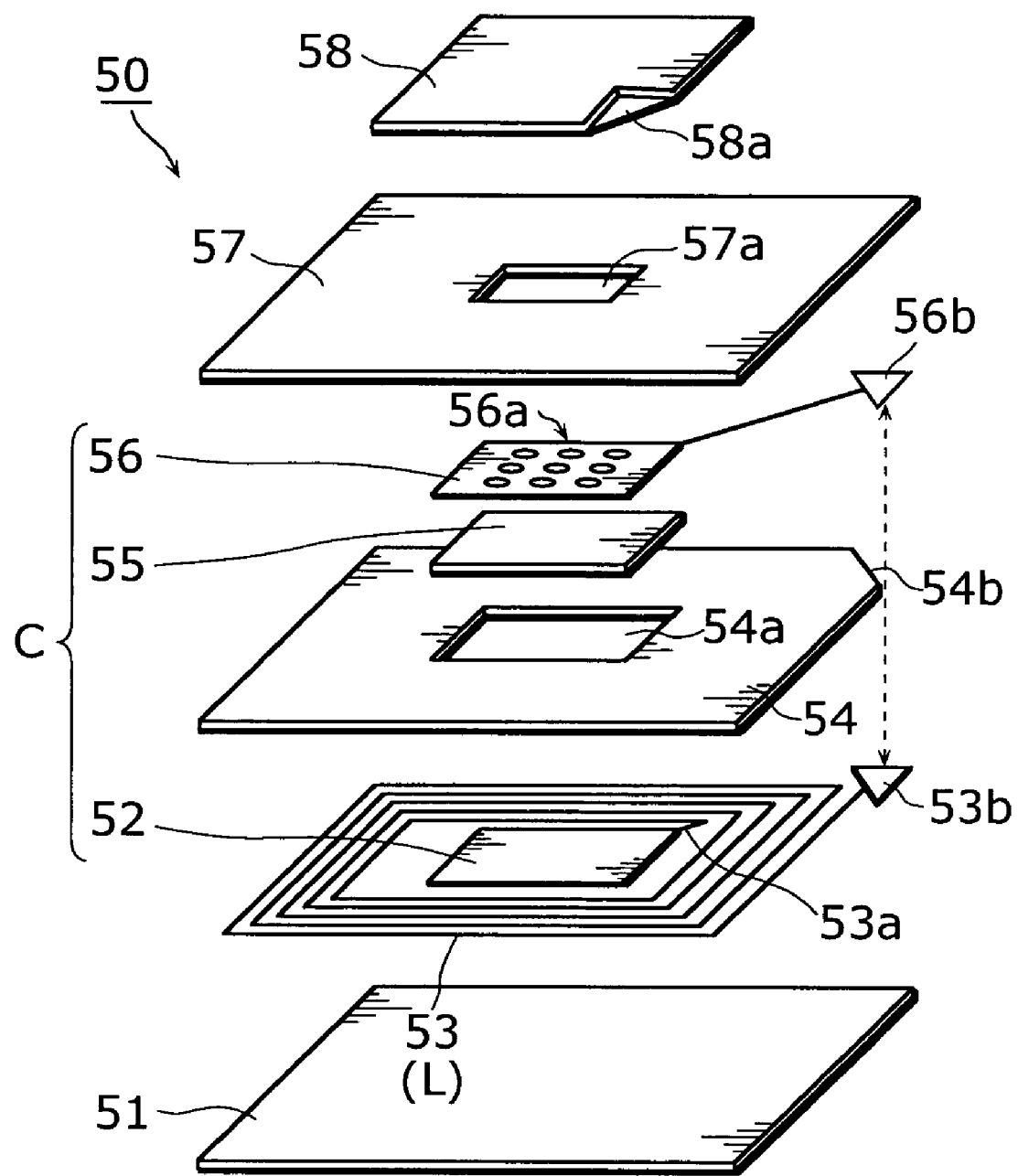
FIG. 3 is an exploded perspective view of the moisture detection sensor 50 shown in FIG. 1 and FIG. 2.

FIG. 3 is an exploded perspective view of the moisture detection sensor 50 shown in FIG. 1 and FIG. 2.

As shown in FIG. 3, the moisture detection sensor 50 further includes an antenna coil 53 affixed on the lower surface of the substrate 54, a pair of electrodes 52 and 56, and the dielectric 55 interposed between these electrodes 52 and 56 in addition to the above-mentioned substrate 54, the covering materials 51 and 57, and the moisture-proof cover 58. There is a square shaped window 54a in a center part of the substrate 54, and a notch 54b is formed at one of the corners of the substrate 54.

The antenna coil 53 is made of a piece of a strip wire that is wound up multiple times, and, for example, formed to achieve 3 µH.

The pair of electrodes 52 and 56 are formed in almost the same size as the window 54a, and are respectively located on the upper surface and the lower surface of the substrate 54. The dielectric 55 is made from a material containing a water-absorbing property and a drainage property (for example, a cotton cloth or paper), and is formed in almost the same size and thickness as the electrodes 52 and 56. The capacitor C is formed by the pair of electrodes 52 and 56 and the dielectric 55. A plurality of pores 56a are formed at the electrode 56 for leading moisture to the dielectric 55. This capacitor C has, for example, approximately 40 pF capacitance when the dielectric 55 is dry.

The first end 53a of the antenna coil 53 is electrically connected to the electrode 52. The second end of the antenna coil 53 is electrically connected to a connection terminal 53b located at a position corresponding to the notch 54b. On the other hand, the electrode 56 is electrically connected to a connection terminal 56b located on a board corresponding to the notch 54b. Both of the connection terminals 53b and 56b are electrically connected to each other by caulking, pressure welding or the like at the position of the notch 54b. As a result, this capacitor C is connected in series to the antenna coil 53, and a resonant circuit is formed at both.

Figure 4:
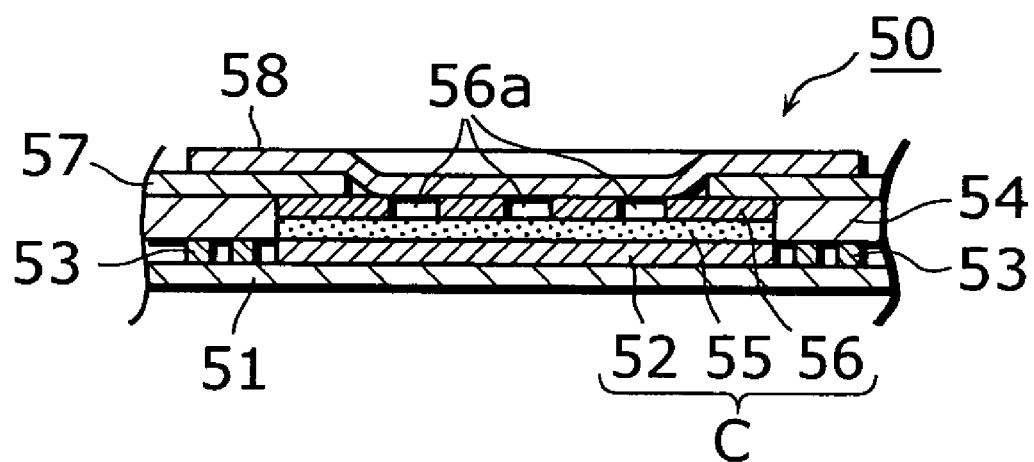
FIG. 4 is a partly expanded sectional view of the moisture detection sensor, which is cut off at A—A shown in FIG. 2A.

FIG. 4 is a partly expanded sectional view of the moisture detection sensor 50, which is cut off at A—A shown in FIG. 2 A.

As shown in FIG. 4, when the moisture-proof cover 58 is affixed, the dielectric 55 keeps a dry condition due to this moisture-proof cover 58. Under this condition, the capacitor C keeps the above capacitance, and the resonant frequency of the resonant circuit, which is formed by the antenna coil 53 and the capacitor C, maintains a specific value. Contrary to this, in a case in which the moisture-proof cover 58 is removed, the moisture detection sensor 50 is inserted into the pocket on the diaper, and there is urination. This urine is promptly absorbed by the dielectric 55 via the through-hole and the pore 56a. When the dielectric 55 absorbs the urine, as the amount of its absorption gets bigger, a relative permittivity between the electrodes 52 and 56 becomes bigger and the capacitance of the capacitor C increases. As a result of this, the resonant frequency of the resonant circuit formed by the antenna coil 53 and the capacitor C declines below a specific value. Therefore, as long as the detection radio wave is emitted from the moisture detection apparatus 10 and a fluctuation in the resonant frequency of the moisture detection sensor 50 is detected, it is possible to detect whether the dielectric 55 is wet or dry.

Figure 5:
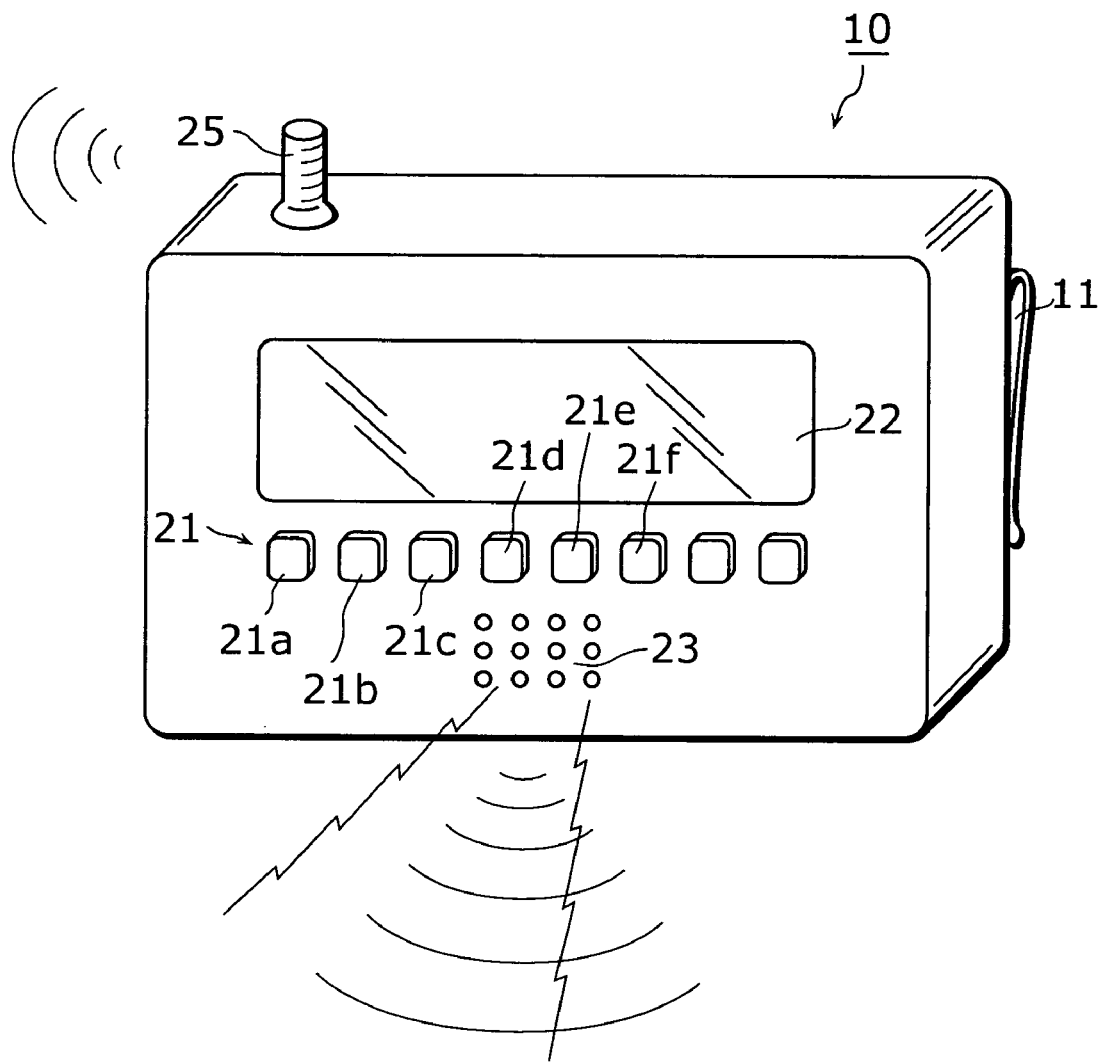
FIG. 5 is a diagram showing an external configuration of a moisture detection apparatus 10 shown in FIG. 1.

FIG. 5 is an external configuration of the moisture detection apparatus 10 shown in FIG. 1.

In addition to the above clip 11, there are an operation unit 21 composed of a plurality of buttons, an LCD unit 22 for displaying guidance, alarms and the like, a speaker 23 for emitting the alarms and the like by sounds, and an antenna 25 for sending data wirelessly to a host (not shown) or the like on a surface of the moisture detection apparatus 10.

The operation unit 21, for example, is composed of a plurality of buttons such as a wetness detection button 21a for setting the moisture detection apparatus 10 to have the moisture detection sensor 50 detect any liquid, a moisture detection button 21b for setting the moisture detection apparatus 10 to have the moisture detection sensor 50 detect that it is getting moistened, a dryness detection button 21c for detecting the moistened moisture detection sensor 50 is getting dry, a detection start button 21d, a detection stop button 21e, and a reset button 21f.

Figure 6:
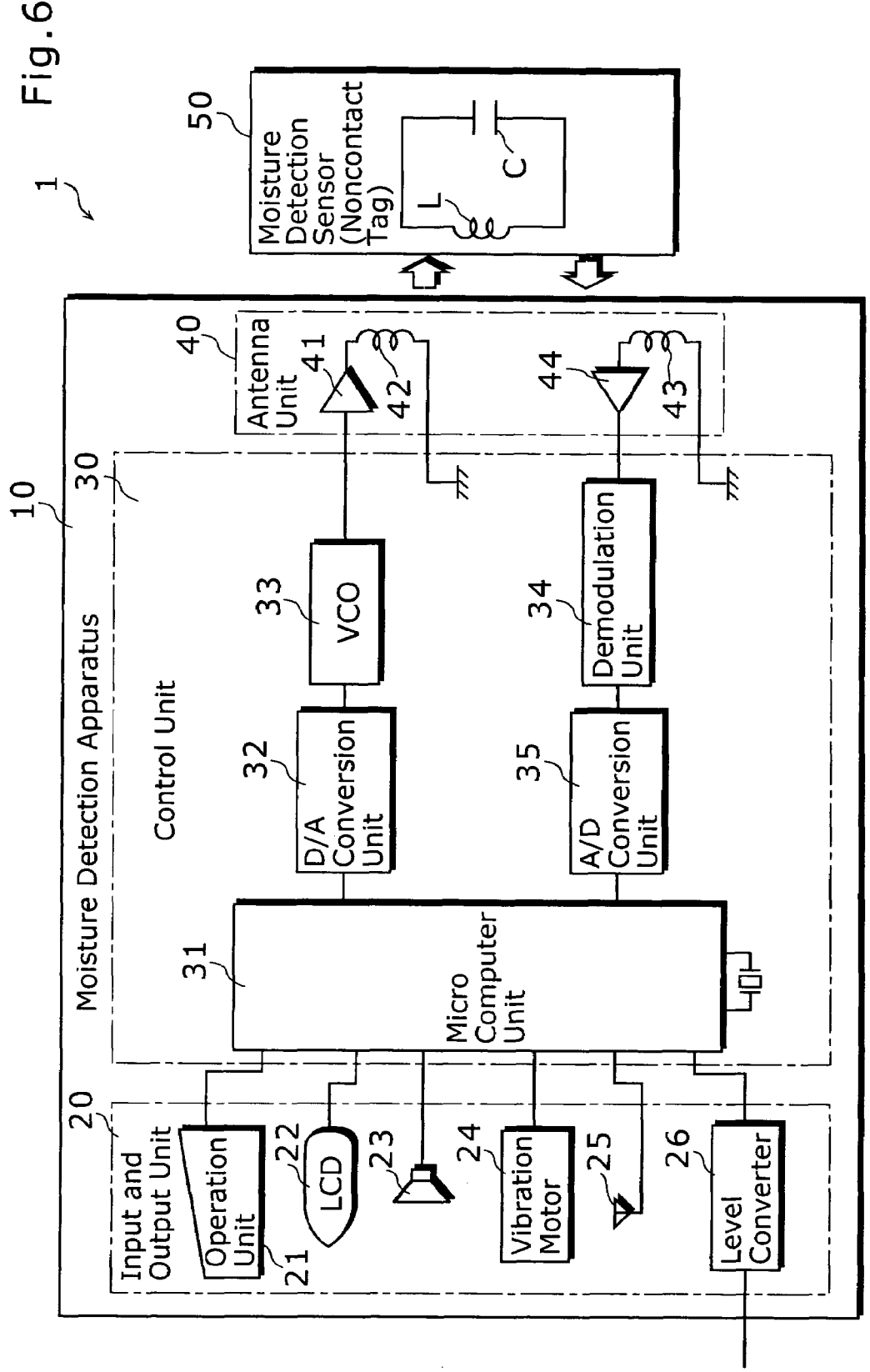
FIG. 6 is a diagram showing an electric configuration of the moisture detection sensor 50 and the moisture detection apparatus 10 shown in FIG. 1.

FIG. 6 is a diagram showing an electric configuration of the moisture detection sensor 50 and the moisture detection apparatus 10.

The moisture detection sensor 50 includes a noncontact tag that forms, with components shown in FIG. 2, an LC resonant circuit composed of the antenna coil L and the capacitor C of which capacitance is changed by moisture.

The moisture detection apparatus 10 is roughly composed of an input and output unit 20, a control unit 30 and an antenna unit 40.

The input and output unit 20 includes the operation unit 21, the LCD unit 22, the speaker 23 for announcing incontinence or the like with sounds, a vibration motor 24 for indicating incontinence or the like to the person who needs care, an antenna 25 for wirelessly informing incontinence or the like of the care recipient to the care giver who is away from the care recipient, and a level converter 26 for sending various data such as time when the diaper has been exchanged, or time when incontinence or the like happens, to a host computer (not shown in the diagrams).

The control unit 30 includes the following elements: ROM that pre-stores a program; a nonvolatile memory (S-RAM or the like) that temporarily holds data such as the resonant frequency of the moisture detection sensor 50 measured in an initialization mode, and data of button types of the operation unit 21 operated by the care-giver or the like; a volatile memory (D-RAM or the like) that provides a working area at the time of program execution; a timer that clocks time; a micro computer unit 31 composed of a CPU and the like for executing the pre-stored program, which is formed in a chip, a D/A conversion unit 32, a VCO (Voltage-Controlled Oscillator) 33 as an oscillator that changes an oscillation frequency, for example around 13.56 MHz, by voltage applied, a demodulation unit 34 that demodulates a radio wave received by the antenna unit 40, and an A/D conversion unit 35.

The antenna unit 40 includes an amplifier 41 that amplifies a transmission signal output from the VCO 33, a transmitting antenna coil 42 that converts the transmission signal amplified by the amplifier 41 into a radio wave and emits the radio wave, a receiving antenna coil 43 that converts the radio wave received from the moisture detection sensor 50 into an electric signal, and an amplifier 44 that amplifies the electric signal received by the receiving antenna coil 43.

Figure 7:
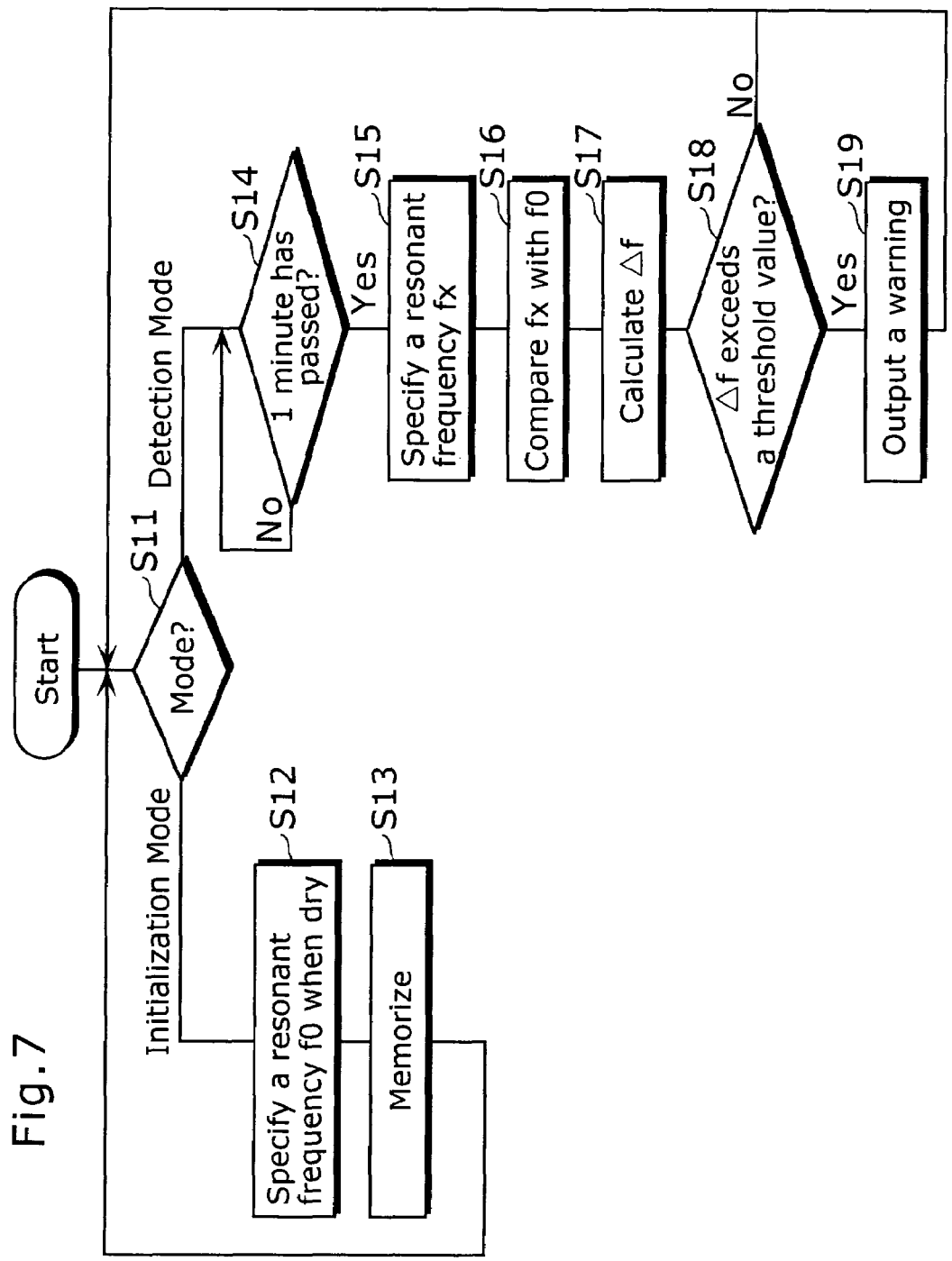
FIG. 7 is a flow chart showing processes executed by a micro computer unit 31 shown in FIG. 6.

FIG. 7 is a flow chart that shows a flow of detection processes executed by the micro computer unit 31 shown in FIG. 6 in a wetness detection mode for detecting wetness of the moisture detection sensor 50.

The micro computer unit 31 at first decides whether or not its mode is the initialization mode for detecting the resonant frequency in a situation in which the dielectric is dry (S11). This decision is made, for example, for a case in which a person to be detected or the care-giver operates the apparatus with a specific button to acquire the resonant frequency under the situation in which the dielectric is dry. The operation here is meant to be, for example, operations such as pressing down the reset button 21$f$ for clearing the resonant frequency detected when the dielectric is dry, and stored in the nonvolatile memory, pressing down the wetness detection button 21$a$ for executing the wetness detection mode, and pressing down the detection start button 21$d$ for starting a process for this wetness detection mode.

For a case in which a specific operation button is operated, and the resonant frequency is cleared from the nonvolatile memory, the micro computer unit 31 executes the initialization mode, specifies a resonant frequency f0 under the situation in which the dielectric is dry (S12), memorizes the specified resonant frequency f0 in its internal memory (S13), and terminates a routine process for this initialization mode.

Figure 8:
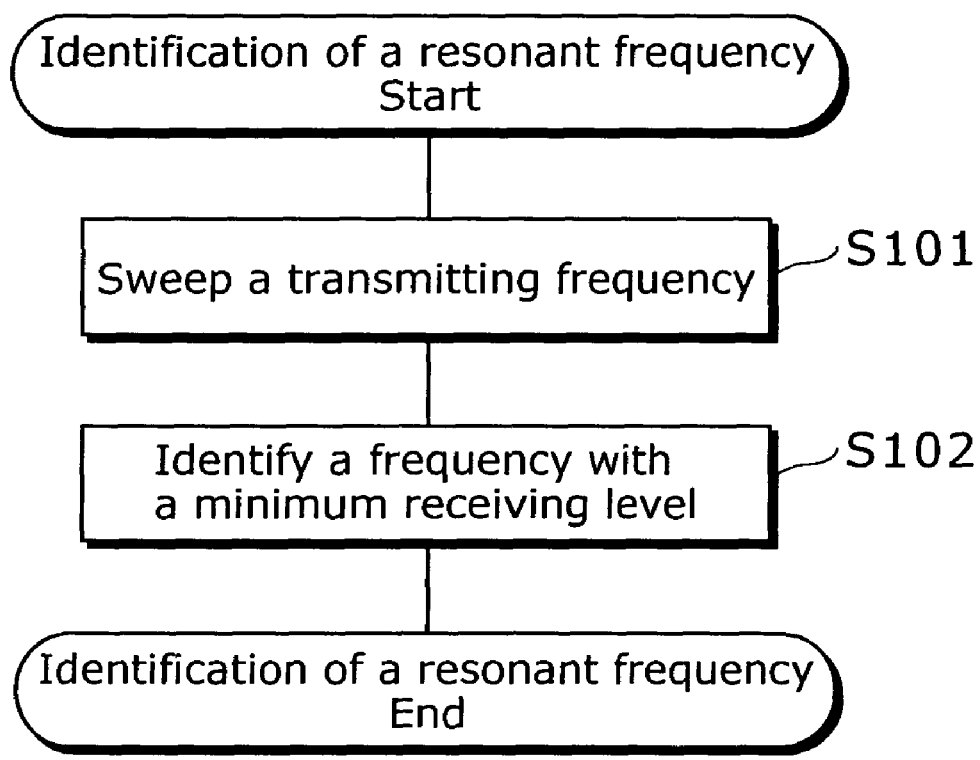
FIG. 8 is a flow chart showing a sub-routine of processes executed for identifying a resonant frequency in a step S12 and a Step S15 in FIG. 7.

This resonant frequency f0 is specified by executing a sub-routine shown in FIG. 8. Specifically, the micro computer unit 31 sweeps the frequency of the detection radio wave emitted from the transmitting antenna coil 42 (S101, See FIG. 9B), and identifies the resonant frequency f0 as a frequency whose radio wave receiving level received by the receiving antenna coil 43 hits a lowest level. (S102, See a solid line of FIG. 9A).

Sweeping the transmitted frequency is achieved by, for example, gradually increasing a digital value which is output from the micro computer unit 31 from a specific value to a bigger specific value, gradually raising voltage input to the VCO 33, and gradually raising the frequency of the signal output from the VCO 33. When the transmitted frequency is swept in this way, the receiving level of the radio wave received by the receiving antenna coil 43 rapidly falls down from a certain value just before a certain frequency (f0), becomes a minimum value at f0, and then rapidly goes up after the frequency f0 and goes back to the certain value. It means a dip phenomenon occurs. Therefore, the resonant frequency when dry can be easily specified as the digital value (the transmitted frequency) output from the micro computer unit 31 when the dip is received.

On the other hand, when the resonant frequency is held in the nonvolatile memory, a detection mode is repeatedly executed for detecting a wet condition of the moisture detection sensor 50 by comparing the resonant frequency f0 when dry with the resonant frequency fx at a point in time. In this detection mode, the micro computer unit 31 at first starts to clock with its internal timer, and waits until a certain period of time elapses (e.g. one minute) (S14).

Figure 9A:
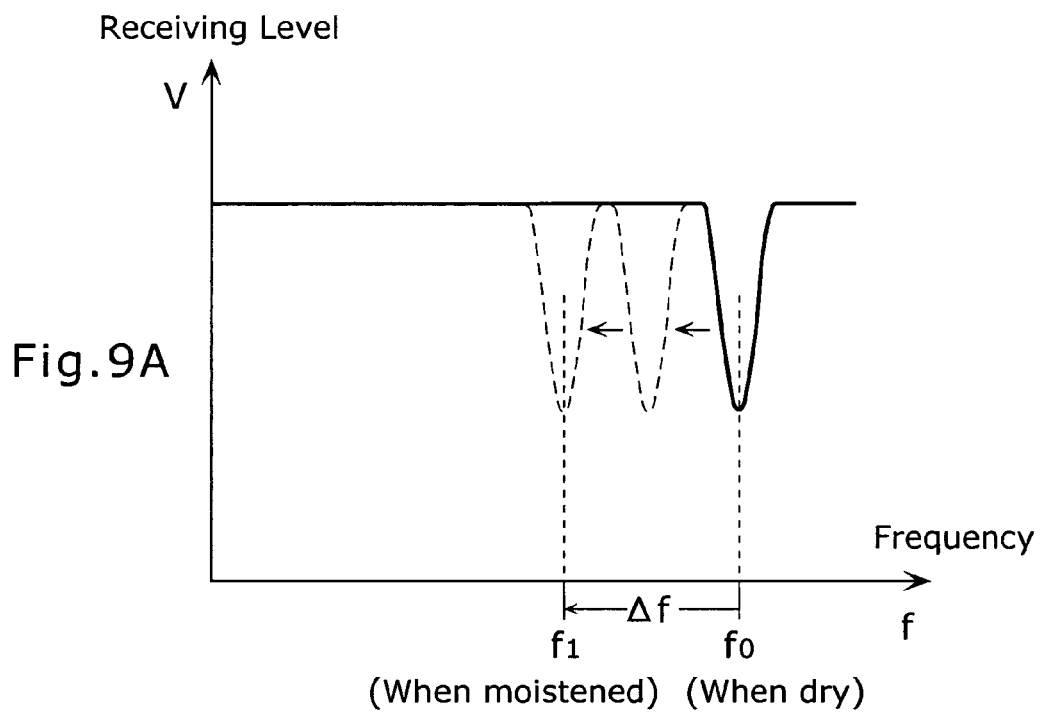
FIG. 9 is a diagram showing a relationship between a receiving level and a frequency detected by the micro computer unit 31.
Figure 9B:
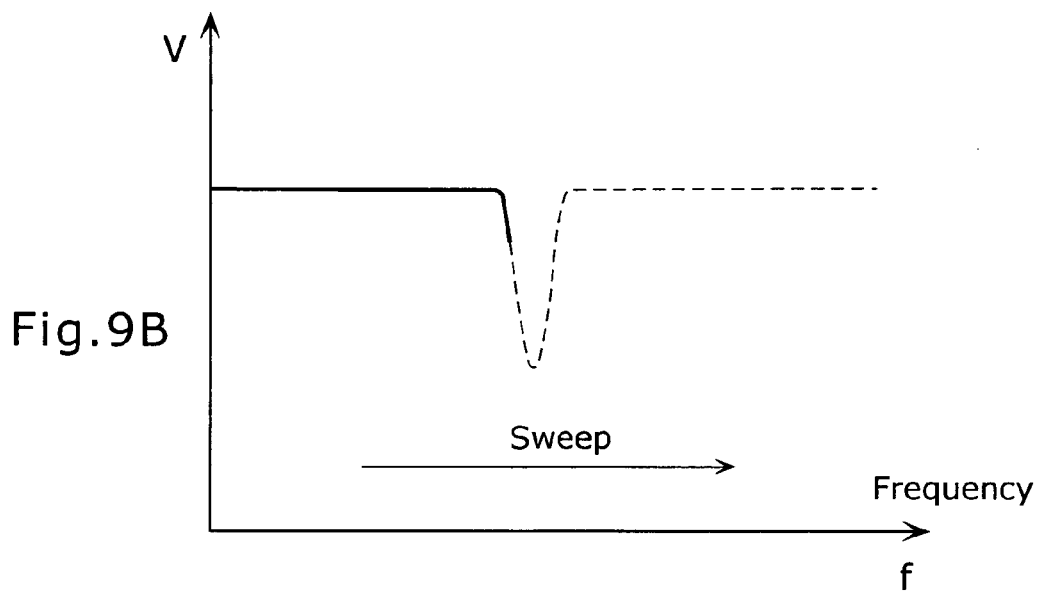

After one minute (Yes in S14), the micro computer unit 31 specifies the resonant frequency fx at the point in time by executing the sub-routine (S101 and S102) (S15, See a dotted line in FIG. 9A). Then, the micro computer unit 31 compares the specified resonant frequency fx with the resonant frequency f0 memorized in the nonvolatile memory (S16), calculates $\Delta f$ ($\Delta f = f0 - fx$) for a shifting amount of the frequency (an amount of moisture) (S17, See FIG. 9A), and decides whether the shifting amount $\Delta f$ exceeds a predetermined threshold value or not (S18). When the shifting amount $\Delta f$ does not exceed the predetermined threshold value (No in S18), the micro computer unit 31 decides that the wet condition of the moisture detection sensor 50 (the diaper 3) is at an acceptable level, and repeatedly executes the Steps S11 and S14 to S18 until it exceeds the threshold value.

Then, when the shifting amount $\Delta f$, which is a shift from the resonant frequency f0 detected when dry and stored in the memory to the resonant frequency fx detected at the time of getting wet, exceeds the predetermined threshold value (Yes in S18), the micro computer 31 decides the wet condition of the moisture detection sensor 50 (the diaper 3) has exceeded the acceptable level, outputs a warning or the like (S 19) by a sound through the speaker 23, by vibration through the vibration motor 24 and through a wireless communication from the antenna 25 to the host computer (S19), and repeatedly executes the Steps S11, S14 to S19 until the care recipient or the care-giver stops the warning through a specific operation button (e.g. the detection stop button 21$e$). The care recipient or the care-giver who recognizes the incontinence through the warning replaces the wet diaper 3.

When the diaper 3 is replaced with a new one, the moisture detection sensor 50 is removed from the pocket 3$a$ of the diaper 3 to be replaced, separated from the diaper 3, and disposed in a way desirable for environmental sanitation, or individually reused after it is washed and dried.

As mentioned above, according to the invention related to the first embodiment, the moisture detection sensor 50 may be structured to be compact and inexpensive because a switch like the one in the conventional arts is not necessary and can be substituted for by the dielectric 55. Besides, the moisture detection sensor 50 can be recycled by washing and drying it after its use. Also, even when the resonant frequency is dispersed because of the reused moisture detection sensor 5, the moisture detection apparatus 10 can make various comparisons such as a comparison of levels when the resonant circuit is formed. Therefore, it can accurately detect the condition of the moisture detection sensor 50.

Figure 10:
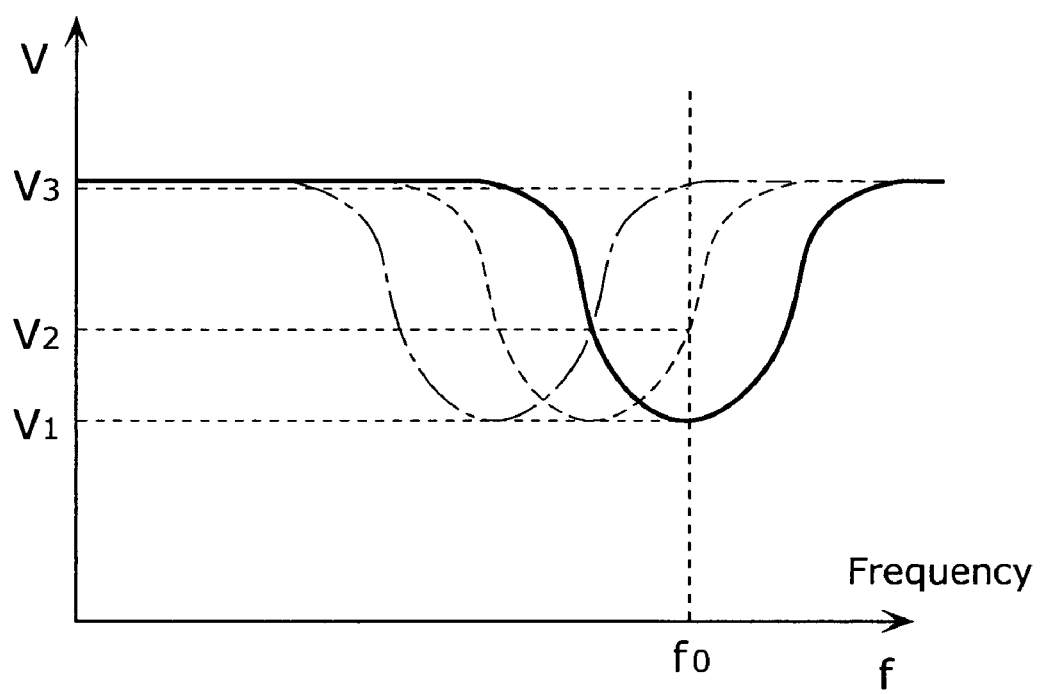
FIG. 10 is a diagram showing another relationship between a receiving level and a frequency detected by the micro computer unit 31.

In the first embodiment, the transmitted frequency is swept. However, as a variation of this embodiment, the receiving level may be detected with a fixed transmitted frequency, which is as shown in FIG. 10, and the moisture may be detected based on this receiving level.

In a case of this variation, it is preferable that the moisture is detected at the receiving level of the transmitted frequency after a digital value output from the micro computer unit 31 is adjusted to have the transmitted frequency be matched with the resonant frequency f0 in the moisture detection sensor. After starting the moisture detection, even though the digital value output from the micro computer unit 31 is fixed and the transmitted frequency stays the same (such as f0), the resonant frequency of the moisture detection sensor 50 becomes lower than f0 as a moistened level of the dielectric 55 goes up. As a result, the receiving level at the frequency f0 goes up from V1 to V2. Then, when the moistened level of the dielectric 55 becomes even higher, the resonant frequency of the moisture detection sensor 50 becomes even lower than f0. As a result, the receiving level of the frequency f0 goes up from V2 to V3. Therefore, it is ensured that wetness of the dielectric 55 in the moisture detection sensor 50 can be detected even by finding the receiving level with the fixed frequency f0.

Second Embodiment

The following describes a configuration of another moisture detection sensor related to a second embodiment of the present invention.

In the moisture detection sensor 50 related to the first embodiment mentioned above, the pocket 3a is formed on the diaper 3, and the moisture detection sensor 50 is inserted into this pocket 3a. In this case, it requires extra work because an opening part of the pocket 3a needs to be opened to attach the moisture detection sensor 50.

Figure 11:
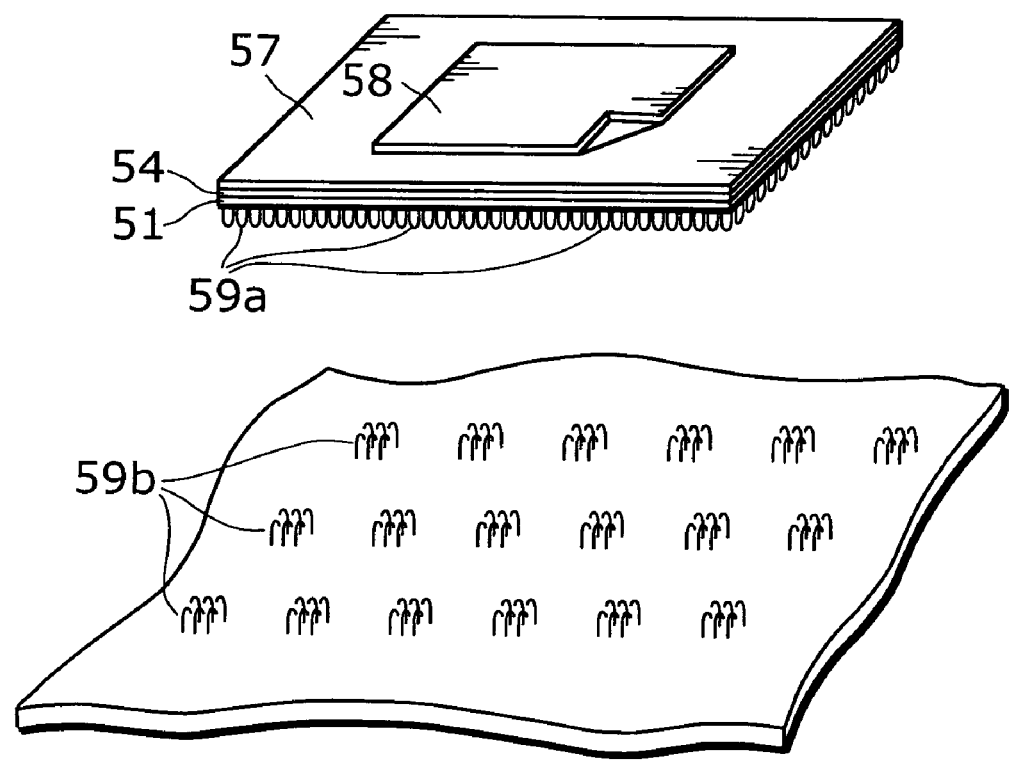
FIG. 11 is a diagram showing a configuration for attaching the moisture detection sensor 50 to a diaper 3.

Therefore, as shown in FIG. 11, the moisture detection sensor 50 related to the second embodiment is structured so that it can be attached by a planar fastener. In particular, one surface of the planar fastener (e.g. a loop material 59a) is attached to a lower surface of the covering material 51 and the other surface of the planar fastener (e.g. a hook material 59b) is attached to the diaper 3, which allows the moisture detection sensor 50 to be attached and detached easily. Therefore, unlike the first embodiment, it is not necessary to open the opening part of the pocket 3a and attach the moisture detection sensor 50. A user can instantly attach and detach the moisture detection sensor 50, which can largely avoid any extra work.

Third Embodiment

The following describes a configuration of another moisture detection sensor related to a third embodiment of the present invention.

In the moisture detection sensor 50 related to the first and second embodiments, the antenna coil 53 in a planar shape is formed on a plane surface. In this structure, when an antenna surface of the moisture detection apparatus 10 is located in parallel with a tag surface formed by the antenna coil 53, a maximum communication range is obtained. In other words, within a certain distance, when the antenna surface and the tag surface are located in parallel, a maximum electromagnetic induction is generated, and there is a direction dependency in detection sensitivity. Therefore, when the tag leans to one side, the electromagnetic induction level falls down, and it may be difficult to specify the resonant frequency in the initialization mode or in the detection mode.

The moisture detection sensor related to the third embodiment of the present invention is intended to resolve issues of the above direction dependency by forming a three-dimensional antenna coil.

Figure 12A:
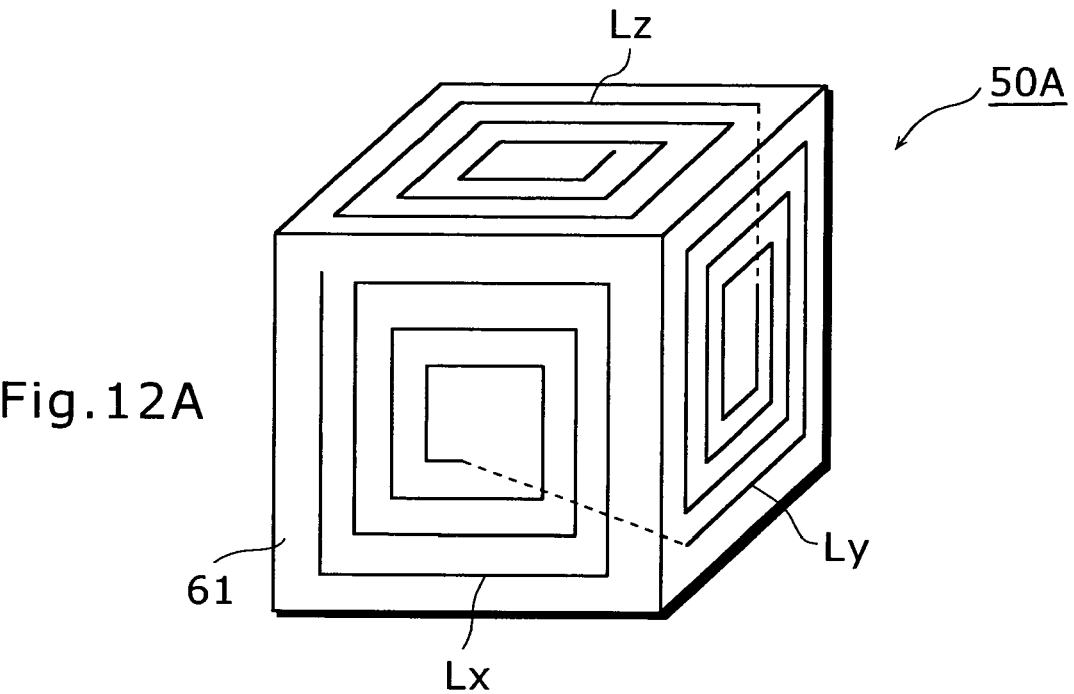
FIG. 12 is a diagram showing a configuration of a moisture detection sensor 50A related to a third embodiment of the present invention.
Figure 12B:
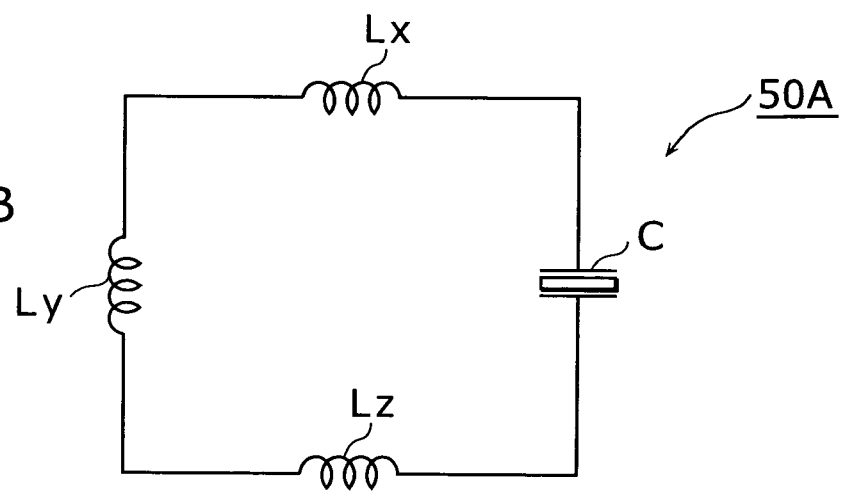

FIG. 12 is a diagram showing a configuration of a moisture detection sensor 50A related to the third embodiment of the present invention. Specifically, FIG. 12 A shows an oblique perspective diagram of a mechanical configuration of the moisture detection sensor 50A, and FIG. 12 B shows a circuit diagram of an electric configuration of the moisture detection sensor 50A. Here, because a main focus is on a three-dimensional configuration of the antenna coil, illustrations of the electrodes 52 and 56 forming a capacitor, the dielectric 55 and so on are omitted in FIG. 12 A.

This moisture detection sensor 50A is composed of, for example, antenna coils (winding faces) Lx~Lz formed respectively on three adjacent surfaces of a compact cube 61 having a length of a few millimeters on each side, and these antenna coils (winding faces) Lx~Lz are connected in series. This cube 61 is made from an insulator material.

When the antenna surface of the moisture detection apparatus 10 is located in parallel with the surface of the antenna coil Lx, electromagnetic induction is generated just between the antenna surface of the moisture detection apparatus 10 and this antenna coil Lx. When the antenna surface of the moisture detection apparatus 10 is located in parallel with the surface of the antenna coil Ly or the surface of the antenna Lz, electromagnetic induction is generated just between the antenna surface and the antenna coil Ly or between the antenna surface and the antenna coil Lz. On the other hand, when the antenna surface of the moisture detection apparatus 10 is deflected from each of the surfaces of the antenna coils Lx~Lz, electromagnetic induction is generated for a sum of a radio wave received by the antenna coils Lx~Lz from the antenna surface. In other words, within a certain distance, whatever angle is created between the antenna surface and the tag surfaces, the electromagnetic induction, which is almost equivalent to the one obtained by having the antenna surface of the moisture detection apparatus 10 set in parallel with an antenna coil, is always generated. Therefore, deterioration of the electromagnetic induction and direction dependency, which occur in the cases of the first and second embodiments, can be avoided, and detection of the resonant frequency is ensured. So, any situation to miss incontinence can be prevented for sure.

In the above embodiment, the antenna coils (winding faces) Lx~Lz are respectively formed only on the three surfaces of the cube, but the antenna coil may also be formed on each of the remaining three surfaces.

Figure 13A:
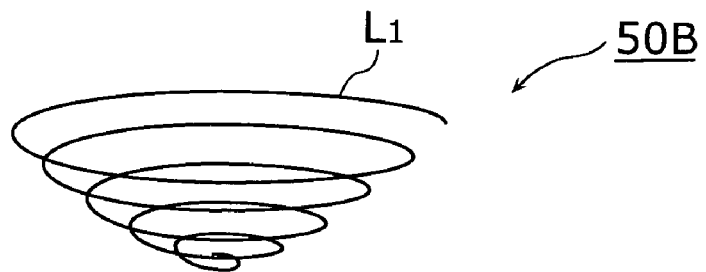
FIG. 13 is a diagram showing a configuration of moisture detection sensors 50B and 50C using another three-dimensional antenna coil.

Also, in the third embodiment, a three-dimensional antenna coil is formed by combining the antenna coils (winding faces) Lx~Lz respectively formed on planar surfaces (i.e., the winding faces are each planar). However, as shown in FIG. 13A, a three-dimensional antenna coil may be formed by building up an antenna coil L1 on a concave surface. In addition, it is also obvious that the three-dimensional antenna may be formed by building up the antenna coil L1 on a convex surface. With such a simple antenna like the antenna coil L1, almost the same effects as those achieved by the antenna coils Lx~Lz can be secured.

Figure 13B:
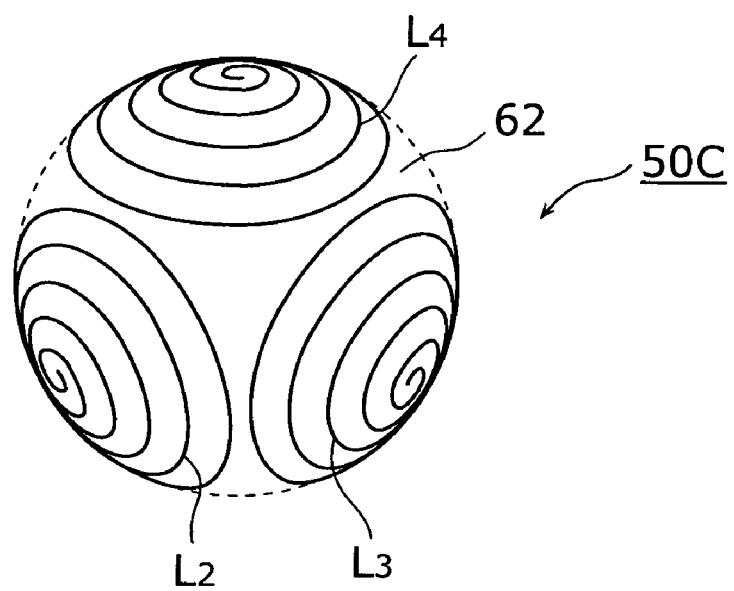

Furthermore, as shown in FIG. 13B, it is possible to form antenna coils L2, L3 and L4 on a sphere surface around X, Y and Z axes having a center of a sphere 62 as an origin of three-dimensional orthogonal coordinates, and the antenna coils L2~L4 may be connected in series.

Even in this case, like the case of the antenna coils Lx~Lz, deterioration of electromagnetic induction, which occurs in the first and second embodiments can be avoided, and detection of the resonant frequency can be ensured. Therefore, any situation to overlook incontinences can be prevented for sure. Also, the antenna coil as a main body may be formed only by a covered conducting wire instead of using a component such as the cube 61 or the sphere 62.

Fourth Embodiment

Figure 14:
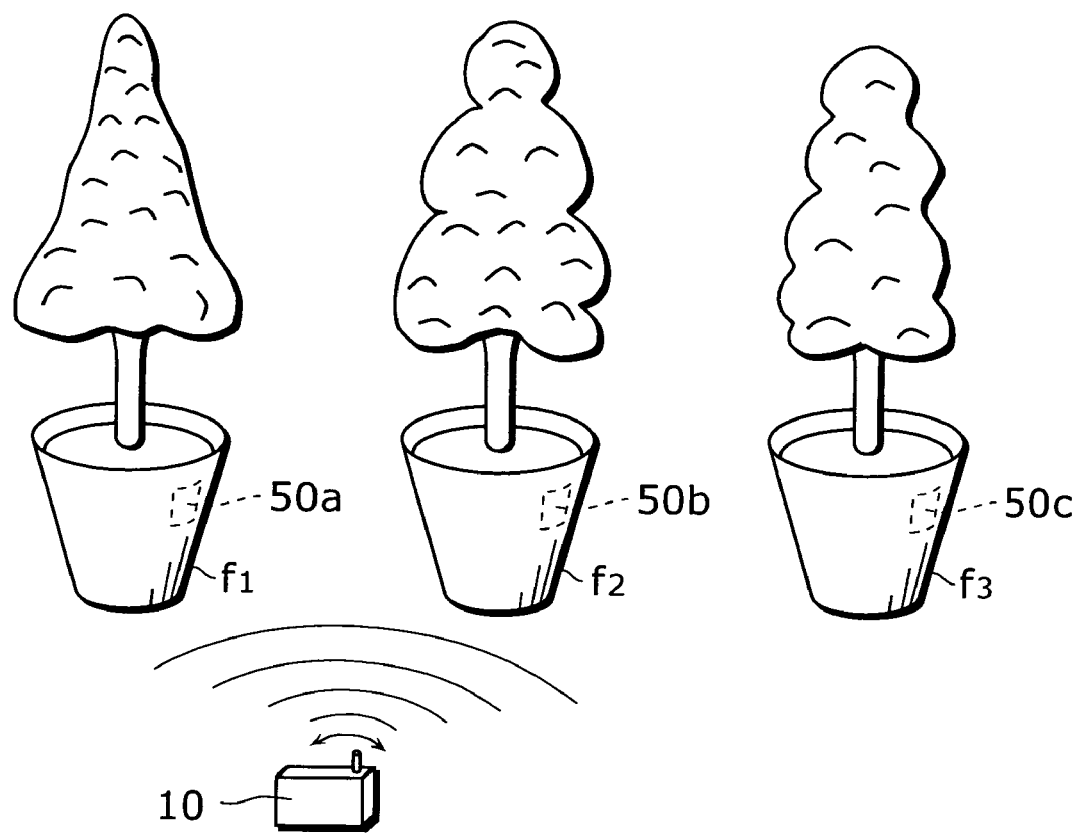
FIG. 14 is a diagram showing an overall configuration for a case in which the moisture detection system 1 related to the present invention is applied to watering management for a plant vase.

FIG. 14 is a diagram showing an overall configuration for a case in which the moisture detection system 1 related to the present invention is applied to watering management for a plant pot.

This moisture detection system 1 applied to the watering management for the plant pot comprises moisture detection sensors 50a~50c respectively attached to each internal bottom surface of plant pots, and the moisture detection apparatus 10 that is configured to respectively and wirelessly detect dryness of soil in each plant pot.

The moisture detection sensors 50a~50c are roughly in the same structure as that of the moisture detection sensor 50 shown in FIG. 2. In this moisture detection system 1, the watering management for each plant pot is performed by a single set of the moisture detection apparatus 10. However, by having different areas of the electrodes 52 and 56 and different numbers of windings for the antenna coil 53 or the like, each of the moisture detection sensors 50a~50c is structured to have a different resonant frequency as f1, f2 and f3 respectively when watering is performed (f'1, f'2 and F'3 when they are dry). Because configurations of other components are the same as those of the first embodiment, their explanation is omitted here.

Next, the following describes how the dryness of the soil in each plant pot is detected.

For detecting the dryness of the soil in each plant pot, the user at first waters each plant pot sufficiently. By doing so, the dielectric 55 for each of the moisture detection sensors 50a~50c absorbs water. Once the watering is done, the user holds the moisture detection apparatus 10 in his hand at a location where a detection radio wave emitted from the moisture detection apparatus 10 reaches the moisture detection sensors 50a~50c respectively in each plant pot, operates the reset button 21f of the moisture detection apparatus 10 and clears the resonant frequency stored in the nonvolatile memory, operates a dryness detection button 21c, and sets the mode to a dryness detection mode that detects dryness based on a condition of the moisture detection sensors 50a~50c when they are wet, and then operates a detection start button 21d to start detecting the resonant frequencies f1, f2 and f3 of the moisture detection sensors 50a~50c when they are wet.

Figure 15:
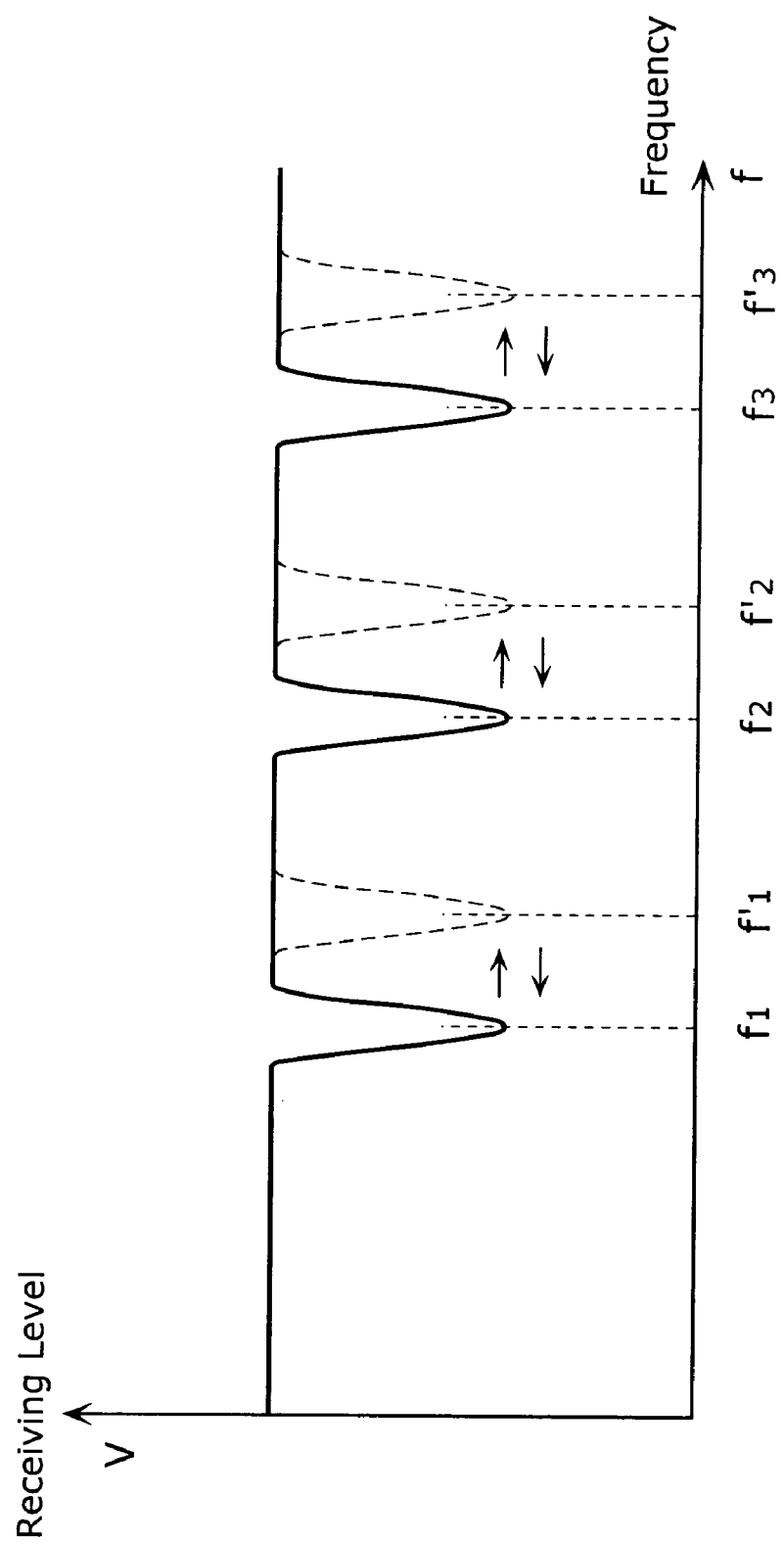
FIG. 15 is a diagram showing a relationship between a receiving level and a frequency detected in the micro computer unit 31.

Once the detection start button 21d is operated, the micro computer unit 31 of the moisture detection apparatus 10 emits from the antenna coil 42 a radio wave that sweeps its frequency, and specifies, from a change in its receiving level (a dip), each resonant frequency (f1, f2 and f3) for a case in which each of the moisture detection sensors 50a~50c absorbs moisture (See a solid line in FIG. 15), and memorizes the specified resonant frequencies f1, f2 and f3 in the nonvolatile memory. When the resonant frequency of each of the moisture detection sensors 50a~50c is specified, the user operates a detection stop button 21e to stop emission of the radio wave.

Once the watering is done, the water in the plant pot is gradually lessened since the plant and the like planted in the pot may absorb the water or the water evaporates as time goes by. In accordance with this, the moisture in the dielectric 55 is lessened. As a result, the resonant frequency of each of the moisture detection sensors 50a~50c becomes gradually higher than the frequency at the time of watering, which is as shown in a dotted line in FIG. 15.

On the following day, when the user is not sure whether he should water the plant or not, he/she only presses the detection start button 21d with the moisture detection apparatus 10 in his hand at the location where the detection radio wave emitted from the moisture detection apparatus 10 reaches the moisture detection sensors 50a~50c located respectively in each plant pot.

Once the detection start button 21d is operated, the micro computer unit 31 emits a radio wave that sweeps its frequency from the antenna coil 42, detects the resonant frequencies (f'1, f'2 and f'3) of each of the moisture detection sensors 50a~50c (See the dotted line in FIG. 15), and individually compares them with the resonant frequencies f1, f2 and f3 that were specified right after watering. As a result of the comparison, when the difference exceeds a threshold value, the apparatus displays the resonant frequency or an ID of the sensor corresponding to the resonant frequency, and outputs a warning sound from its speaker.

Therefore, a plant pot that requires water can be easily detected within a plurality of plant pots, and the plants can be prevented from dying.

In this embodiment, dryness of the soil in the plant pot is detected based on data at the time of watering as its criterion. However, like the case of detecting incontinence, the device may detect whether watering is enough based on data when the soil in the plant pot is dry as its criterion.

Moreover, though explanations are given for the cases of incontinence and watering in the first to fourth embodiments, it is obvious that the present invention may be used for detecting human body fluid using a certain medical apparatus (e.g. sanitary products, bandages, and poultices), underwear, or the like.

What is claimed is:
1. A liquid detection apparatus comprising:
    a liquid detection sensor to be attached to an object to be monitored, said liquid detection sensor comprising:
        a resonant circuit including:
            a coil having at least two winding faces arranged to have a three-dimensional shape; and
            a capacitor having a pair of electrodes and a dielectric interposed between said pair of electrodes; and
        a noncontact tag including a covering material covering said resonant circuit, said covering material having a through-hole for allowing liquid to infiltrate into said dielectric of said resonant circuit;

a detection radio wave emitting unit operable to emit a detection radio wave to said liquid detection sensor by sweeping a frequency of the detection radio wave emitted therefrom;

a radio wave receiving unit operable to receive a radio wave returned from said liquid detection sensor when the detection radio wave is emitted by said detection radio wave emitting unit;

a frequency specifying unit operable to specify a frequency corresponding to a lowest level of the radio wave received by said radio wave receiving unit;

a frequency fluctuation detecting unit operable to detect a fluctuation in the frequency specified by said frequency specifying unit; and a decision unit operable to determine wetness or dryness of the object to be monitored based on an amount of the fluctuation in the frequency specified by said frequency specifying unit.

2. The liquid detection apparatus of claim 1, wherein said detection radio wave emitting unit is operable to emit the detection radio wave continuously.

3. The liquid detection apparatus of claim 1, wherein said detection radio wave emitting unit is operable to emit the detection radio wave intermittently.

4. The liquid detection apparatus of claim 1, wherein said dielectric is a hygroscopic material.

5. The liquid detection apparatus of claim 1, wherein at least one of said electrodes has a pore communicating with said through-hole of said covering material.

6. The liquid detection apparatus of claim 1, wherein said liquid detection sensor further comprises a sealing member detachably attached to an external surface of said covering material so as to block inflow of the liquid into said dielectric via said through hole, and arranged to allow the liquid to infiltrate into said dielectric when removed.

7. The liquid detection apparatus of claim 1, wherein said liquid detection sensor has a planar quadrilateral shape.

8. The liquid detection apparatus of claim 1, further comprising a planar fastener attached to said covering material for attaching said liquid detection sensor to the object to be monitored.

9. The liquid detection apparatus of claim 1, wherein at least one of said winding faces of said coil is wound in a spiral shape.

10. The liquid detection apparatus of claim 1, wherein said coil is arranged so that at least two of said winding faces are orthogonal to each other.

11. The liquid detection apparatus of claim 1, wherein said coil has three winding faces arranged so that said three winding faces are orthogonal to each other.

12. The liquid detection apparatus of claim 1, wherein each of said at least two winding faces of said coil is planar.

13. The liquid detection apparatus of claim 1, wherein each of said at least two winding faces of said coil is three-dimensional.

14. The liquid detection apparatus of claim 13, wherein each of said at least two winding faces of said coil is formed on one of a concave surface and a convex surface.

15. A liquid detection sensor comprising:
a resonant circuit including:
a plurality of coils connected in series, each of said coils having a winding face so that said plurality of coils has a plurality of winding faces, said winding faces being arranged in a three-dimensional manner and so that at least two of said winding faces are orthogonal to each other; and
a capacitor connected to said coils in parallel, said capacitor having a pair of electrodes and a dielectric interposed between said pair of electrodes; and
a noncontact tag including a covering material covering said resonant circuit, said covering material having a through-hole for allowing liquid to infiltrate into said dielectric of said resonant circuit.

16. The liquid detection sensor of claim 15, wherein said dielectric is a hygroscopic material.

17. The liquid detection sensor of claim 15, wherein at least one of said electrodes has a pore communicating with said through-hole of said covering material.

18. The liquid detection sensor of claim 15, further comprising a sealing member detachably attached to an external surface of said covering material so as to block inflow of the liquid into said dielectric via said through hole, and arranged to allow the liquid to infiltrate into said dielectric when removed.

19. The liquid detection sensor of claim 15, wherein said liquid detection sensor has a planar quadrilateral shape.

20. The liquid detection sensor of claim 15, further comprising a planar fastener attached to said covering material for attaching said liquid detection sensor to an object.

21. The liquid detection sensor of claim 15, wherein said plurality of coils comprises three coils each having a winding face so that said three coils have three winding faces, said three winding faces being arranged orthogonal to each other.

22. The liquid detection sensor of claim 15, wherein each of said winding faces is planar.

23. The liquid detection sensor of claim 15, wherein each of said winding faces is three-dimensional.

24. The liquid detection sensor of claim 23, wherein each of said winding faces is formed on one of a concave surface and a convex surface.

* * * * *